US007750325B2

(12) United States Patent
Akers

(10) Patent No.: US 7,750,325 B2
(45) Date of Patent: Jul. 6, 2010

(54) METHODS AND APPARATUS FOR PRODUCING AND STORING POSITRONS AND PROTONS

(75) Inventor: Douglas W. Akers, Idaho Falls, ID (US)

(73) Assignee: The United States of America as represented by the United States Department of Energy, Washington, DC (US)

(*) Notice: Subject to any disclaimer, the term of this patent is extended or adjusted under 35 U.S.C. 154(b) by 365 days.

(21) Appl. No.: 11/946,512

(22) Filed: Nov. 28, 2007

(65) Prior Publication Data

US 2009/0134344 A1 May 28, 2009

(51) Int. Cl.
*G21G 4/00* (2006.01)
*G21G 5/00* (2006.01)
*A61N 5/00* (2006.01)
*G01J 1/00* (2006.01)

(52) U.S. Cl. ............... 250/493.1; 250/492.1; 250/503.1

(58) Field of Classification Search ......... 250/281–287, 250/492.1, 493.1, 503.1, 428, 432, 496.1
See application file for complete search history.

(56) References Cited

U.S. PATENT DOCUMENTS 3,670,494 A * 6/1972 Papp .......................... 376/320
3,970,855 A * 7/1976 Holt et al. ................ 250/493.1
4,365,160 A * 12/1982 Mills, Jr. .................. 250/503.1
4,835,390 A * 5/1989 Blatchley et al. ......... 250/360.1
4,933,950 A * 6/1990 Ikegami ....................... 372/73
5,159,195 A * 10/1992 Van House .................. 250/306
5,530,245 A * 6/1996 Huang ........................ 250/307
5,583,896 A * 12/1996 Hirose et al. ................ 376/195
6,178,218 B1 * 1/2001 Akers et al. ............ 250/363.03
6,635,871 B2 * 10/2003 Xu et al. ..................... 250/309
6,815,676 B2 * 11/2004 Shirai et al. ................. 250/307
7,041,508 B2 * 5/2006 Smith ......................... 436/104

(Continued)

FOREIGN PATENT DOCUMENTS

JP 01165943 A * 6/1989

OTHER PUBLICATIONS

Greaves, R and Surko, C.M. "An Electron-Positron beam plasma experiment" Phys. Rev. Letters, vol. 75, No. 21, Nov. 20, 1995. pp. 3846-3849.*

(Continued)

*Primary Examiner*—Jack I Berman
*Assistant Examiner*—Brooke Purinton
(74) *Attorney, Agent, or Firm*—Michael J. Dobbs; Daniel D. Park

(57) ABSTRACT

Apparatus for producing and storing positrons may include a trap that defines an interior chamber therein and that contains an electric field and a magnetic field. The trap may further include a source material that includes atoms that, when activated by photon bombardment, become positron emitters to produce positrons. The trap may also include a moderator positioned adjacent the source material. A photon source is positioned adjacent the trap so that photons produced by the photon source bombard the source material to produce the positron emitters. Positrons from the positron emitters and moderated positrons from the moderator are confined within the interior chamber of the trap by the electric and magnetic fields. Apparatus for producing and storing protons are also disclosed.

36 Claims, 3 Drawing Sheets

U.S. PATENT DOCUMENTS

| | | | | |
|---|---|---|---|---|
| 2001/0040223 | A1* | 11/2001 | Fujiwara et al. | 250/493.1 |
| 2002/0030160 | A1* | 3/2002 | Greaves | 250/308 |
| 2003/0043951 | A1* | 3/2003 | Akers | 376/157 |
| 2003/0048864 | A1* | 3/2003 | Akers | 376/157 |
| 2003/0175982 | A1* | 9/2003 | Smith | 436/104 |
| 2003/0177756 | A1* | 9/2003 | Meyer et al. | 60/203.1 |
| 2004/0075052 | A1* | 4/2004 | Shirai et al. | 250/309 |
| 2004/0173745 | A1* | 9/2004 | Uedono et al. | 250/309 |
| 2004/0178353 | A1* | 9/2004 | Perez et al. | 250/427 |
| 2004/0245448 | A1* | 12/2004 | Glish et al. | 250/281 |
| 2005/0061994 | A1* | 3/2005 | Amini | 250/492.1 |
| 2005/0117682 | A1* | 6/2005 | Akers | 376/157 |
| 2007/0110208 | A1* | 5/2007 | Molina-Martinez | 376/100 |
| 2007/0238087 | A1* | 10/2007 | Smith | 250/302 |
| 2008/0156993 | A1* | 7/2008 | Weinberg et al. | 250/363.03 |
| 2010/0012864 | A1* | 1/2010 | Smith | 250/506.1 |

OTHER PUBLICATIONS

Wineland D.J. et al. "Laser cooled positron source" Hyperfine Interactions, vol. 76, (1993), pp. 115-125.*

Tanaka et al. "Slow Positron Production with a Modular Photon Positron Converter attached to a High Current LINAC" Jpn. J. Appl. Phys. vol. 31 (1992) pp. 4029-4036.*

* cited by examiner

METHODS AND APPARATUS FOR PRODUCING AND STORING POSITRONS AND PROTONS

CONTRACTUAL ORIGIN OF THE INVENTION

This invention was made with United States Government support under Contract No. DE-AC07-05ID14517 awarded by the United States Department of Energy. The United States Government has certain rights in the invention.

TECHNICAL FIELD

This invention relates to positron and proton production in general and more specifically to methods and apparatus for producing and storing positrons and protons.

BACKGROUND

Positrons are the anti-matter counterpart to electrons and are used in a wide variety of fields, from particle physics to medicine. Positrons may also be used for power applications, including rockets, because of the high power density associated with positrons. While several methods for producing positrons are known and are being used, the apparatus required to produce and store positrons are cumbersome and expensive. For example, one method for producing positrons involves the use of particle accelerators, which are expensive and difficult to operate. Once the positrons are produced, they must be somehow conveyed to a suitable storage apparatus, such as a Penning-Malmberg trap, for storage and later release. Of course, the anti-matter nature of positrons makes it difficult to convey and store the positrons as they quickly annihilate with conventional matter (i.e., electrons). As a result, only a very small fraction (e.g., 1 in $10^5$) of the positrons actually produced can be conveyed to the storage system.

Another method for producing positrons involves the use of certain radioactive isotopes, such as sodium-22, which produces positrons as a result of radioactive decay. The positrons are then moderated, usually in a tungsten “blind,” and stored in a Penning-Malmberg trap. While the use of such radioactive isotopes as positron sources does away with the need for particle accelerators, they are not without their problems. For example, first are the problems associated with the utilization of the open radioactive source (e.g., Na-22). Second, a large fraction of the positrons are annihilated within the source or the source holder before they can be moderated and stored. Third are the difficulties in transferring the positrons away from the source to the trap.

Consequently, a need remains for a method and apparatus for producing and storing positrons that does not suffer from the disadvantages of current methods.

SUMMARY OF THE INVENTION

Apparatus for producing and storing positrons according to one embodiment of the invention may include a trap that defines an interior chamber therein and that contains an electric field and a magnetic field. The trap may further include a source material that includes atoms that, when activated by photon bombardment, become positron emitters to produce positrons. The trap may also include a moderator positioned adjacent the source material. A photon source is positioned adjacent the trap so that photons produced by the photon source bombard the source material to produce the positron emitters. Positrons from the positron emitters and moderated positrons from the moderator are confined within the interior chamber of the trap by the electric and magnetic fields.

Another embodiment of apparatus for producing and storing positrons may include a generally cylindrically-shaped trap defining an interior chamber therein. The trap includes a source material having atoms that, when activated by photon bombardment, become positron emitters that produce positrons. A moderator positioned within the interior chamber defined by the generally cylindrically-shaped trap moderates positrons emitted by the positron emitters activated within the source material. A voltage source electrically connected to the trap causes an electric field to be established within the interior chamber defined by the trap. A magnet is positioned adjacent the trap so that at least a portion the interior chamber is contained within a magnetic field produced by the magnet.

Still another embodiment of apparatus for producing and storing positrons may include a trap that defines an interior chamber therein. Electric field generation means operatively associated with the trap produces an electric field within the interior chamber of the trap. Magnetic field generation means operatively associated with the trap produces a magnetic field within the interior chamber of the trap. A source material positioned within the interior chamber defined by the trap includes atoms that, when activated by photon bombardment, become positron emitters that produce positrons. A moderator positioned adjacent the source material moderates positrons emitted by the positron emitters activated within the source material. A photon source positioned adjacent the trap produces photons that bombard the source material to produce the positron emitters. Positrons from the positron emitters and moderated positrons from the moderator are confined within the interior chamber of the trap by the electric and magnetic fields.

Still yet another embodiment of apparatus for producing and storing positrons may include a trap defining an interior chamber therein that is adapted to contain an electric field and a magnetic field. A source material provided within the interior chamber of the trap includes atoms that, when activated by photon bombardment, become positron emitters that produce positrons. A moderator positioned adjacent the source material moderates positrons emitted by the positron emitters activated within the source material. A photon source positioned exterior to the trap produces photons that bombard the source material to produce the positron emitters.

Also disclosed is a method for producing and storing positrons that comprises: Providing a trap defining an interior chamber therein, the trap comprising a source material having atoms that, when activated by photon bombardment, become positron emitters that produce positrons; establishing an electric field within the interior chamber defined by the trap; establishing a magnetic field within the interior chamber defined by the trap; and bombarding the source material with photons, the photons activating atoms of the source material to produce the positron emitters, positrons from the positron emitters being confined within the interior chamber of the trap by the electric and magnetic fields.

Another embodiment may be used to produce and store protons and may include a trap defining an interior chamber therein that contains an electric field and a magnetic field. The trap may further include a source material having atoms that, when activated by photon bombardment, become proton emitters that produce protons. A photon source positioned adjacent the trap produces photons that bombard the source material to produce the proton emitters, protons from the proton emitters being confined by the electric and magnetic fields within the interior chamber of the trap.

A method for producing and storing protons may comprise: Providing a trap defining an interior chamber therein, the trap comprising a source material having atoms that, when activated by photon bombardment, become proton emitters that produce protons; establishing an electric field within the interior chamber defined by the trap; establishing a magnetic field within the interior chamber defined by the trap; and bombarding the source material with photons, the photons activating atoms of the source material to produce the proton emitters, protons from the proton emitters being confined within the interior chamber of the trap by the electric and magnetic fields.

BRIEF DESCRIPTION OF THE DRAWING

Illustrative and presently preferred embodiment of the invention are shown in the accompanying drawing in which.

DETAILED DESCRIPTION OF THE PREFERRED EMBODIMENTS

Figure 1:
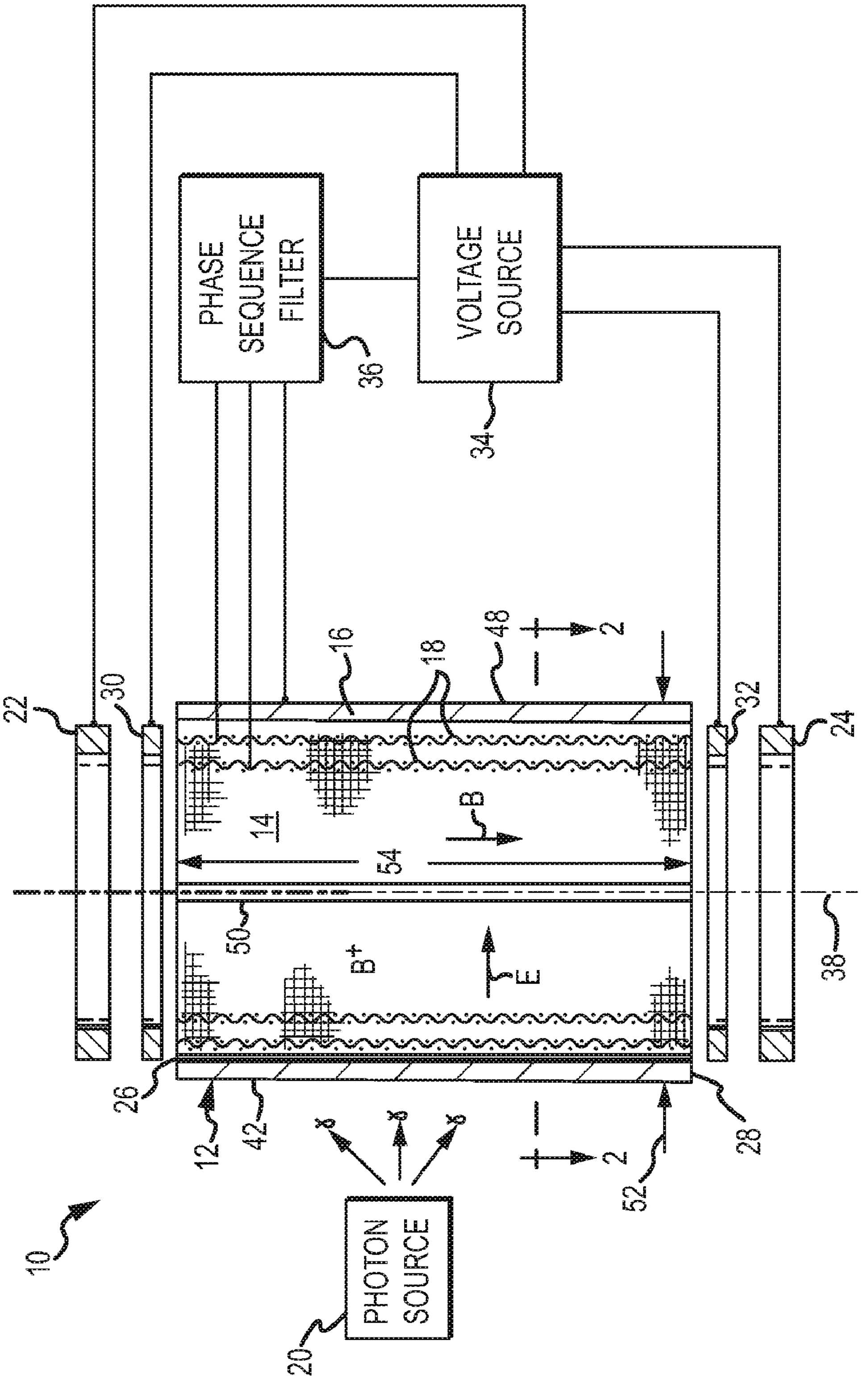
FIG. 1 is a schematic representation of one embodiment of apparatus for producing and storing positrons.
Figure 2:
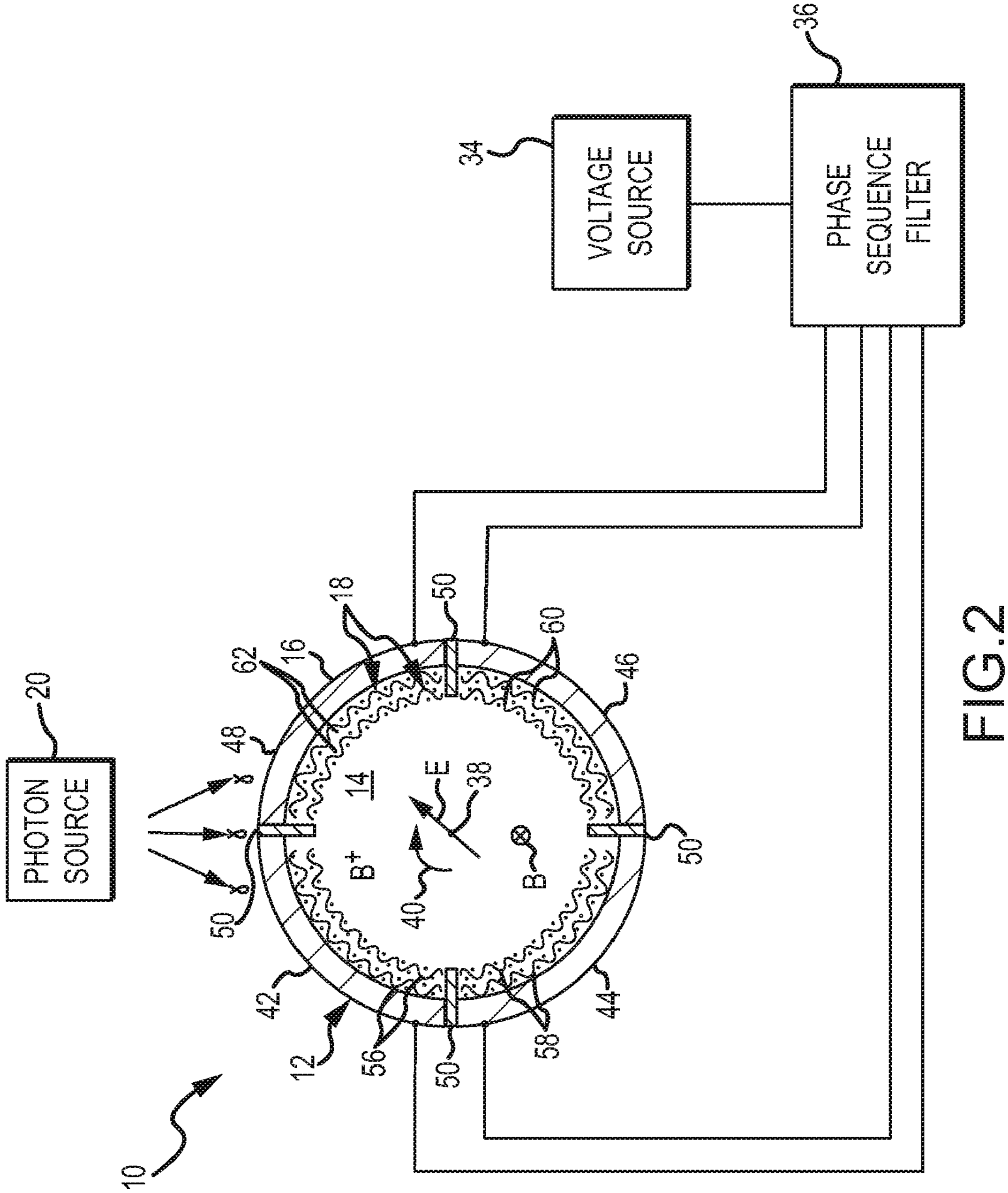
FIG. 2 is a cross-sectional view in elevation of the apparatus for producing and storing positrons taken along the line 2-2 of FIG. 1.

One embodiment of apparatus 10 for producing and storing positrons $\beta^+$ is best seen in FIGS. 1 and 2 and may comprise a trap 12 that defines an interior chamber 14 therein. During operation of the apparatus 10, and as will be described in much greater detail herein, the interior chamber 14 of trap 12 contains a magnetic field B and an electric field E. The magnetic field B and electric field E have strengths, configurations, and orientations suitable for confining positrons $\beta^+$ within the interior chamber 14. The magnetic field B may be produced by a suitable magnet assembly (not shown) located exterior to the trap 12. The electric field E may be produced by applying suitable voltage potentials to the various components of the trap 12. Trap 12 may also comprise a source material 16 containing atoms that, when activated by photon bombardment (schematically illustrated by arrows γ) become positron emitters that produce positrons $\beta^+$. Trap 12 may also comprise a moderator 18 positioned adjacent the source material 16. Moderator 18 moderates positrons $\beta^+$ emitted by the positron emitters within the source material 16. Photons γ suitable for activating the source material 16 may be produced by a photon source 20 positioned adjacent to the trap 12.

Source material 16 may comprise any of a wide range of materials (e.g., metals and various metal alloys) that contain atoms that, when activated by photons γ, become positron emitters (e.g., via the γ,n process). Exemplary materials for the source material 16 include nickel, nickel-tungsten alloys, and copper, although other materials may be used. The moderator 18 may comprise any of a wide range of materials suitable for moderating positrons $\beta^+$ produced by the source material 16. In addition, it is generally preferred, but not required, that moderator 18 also comprise a material that contains atoms that, when activated by photon bombardment, become positron emitters (e.g., via the γ,n process) in order to increase positron yield. By way of example, in one embodiment, the moderator 18 may also be fabricated from nickel, nickel-tungsten alloys, and copper. Silver and various alloys thereof may also be used, as will be described in greater detail herein. Consequently, in one embodiment, both the source material 16 and the moderator 18 produce positrons $\beta^+$.

Trap 12 may also comprise one or more end cap electrodes 22 and 24 positioned adjacent the open ends 26, 28 of trap 12. End cap electrodes 22 and 24 may be used to confine and/or selectively release positrons $\beta^+$ that are confined or trapped within the interior chamber 14 of trap 12. Trap 12 may also comprise a pair of compensating electrodes 30 and 32 positioned between the open ends 26, 28 of trap 12 and the end cap electrodes 22 and 24, as best seen in FIG. 1. The apparatus 10 may also be provided with a voltage source 34 that is electrically connected to the various components of trap 12. More specifically, voltage source 34 may be electrically connected to the source material 16, the moderator 18, the end cap electrodes 22 and 24, as well as the compensating electrodes 30 and 32. Voltage source 34 may be operated to place various voltages and/or time varying voltage functions on the various components to allow the trap 12 to be operated in the various operational modes described herein.

For example, voltage source 34 may be used to apply a trapping voltage function to the various components of trap 12 in order to confine or trap the positrons $\beta^+$ within trap 12. In one embodiment, a phase sequence filter 36 operatively associated with voltage source 34 may be used to cause the electric field E to rotate about an axis 38 of trap 12, as best seen in FIG. 2. The combination of the rotating electric field E and the axially-oriented magnetic field B serves to confine the positrons $\beta^+$ within trap 12. That is, the rotating electric field E causes the positrons $\beta^+$ to enter a Trivelpiece-Gould plasma mode which will cause the positrons $\beta^+$ to be tightly confined along axis 38 of trap 12.

Voltage source 34 may also be operated to apply a release voltage function to the various components of trap 12. The release voltage function will result in the formation of a releasing electric field E that, when combined with magnetic field B, will allow the positrons $\beta^+$ to be released from the trap 12 (e.g., via one or both of the end cap electrodes 22 and 24).

The apparatus 10 may be operated as follows to produce and store for later release a quantity of positrons $\beta^+$. Assuming that the trap 12 has been positioned inside a suitable vacuum chamber (not shown) which has been evacuated to a high vacuum, the source material 14 may be bombarded by photons γ having energies sufficient to activate atoms within the source material 14, thereby causing them to become positron emitters. For example, in an embodiment wherein the source material 16 and moderator 18 comprise copper, photons γ having energies in the range of about 10-20 million electron volts (MeV) will be sufficient to activate the various isotopes of copper comprising source material 16 and moderator 18, thereby causing them to become positron emitters.

In this regard it should be noted that many different activation processes are possible and should be regarded as within the scope of the present invention. For example, and as will be described in further detail below, in another embodiment, the trap 12 may be activated before it is placed within the vacuum chamber. In yet another variation, just the source material portion 16 of trap 12 may be activated, then positioned within the trap 12 which may then be used to confine and/or release trapped positrons. Consequently, the present invention should not be regarded as limited to any particular method or arrangement for bombarding the source material 16 with photons γ.

After the source material 16 and/or moderator 18 have been "activated," i.e., after they have been bombarded by photons γ, the voltage source 34 may be operated to place a trapping voltage function on the various components of the trap 12. For example, in one embodiment, the voltage source 34 may place the trapping voltage function on the various components at some point during the activation process, e.g., at the point where positrons $\beta^+$ are beginning to be produced in significant numbers. Alternatively, the trapping voltage function could be applied after the activation process is complete. In any event, the resulting trapping electric field E, in combination with the magnetic field B, will serve to trap or confine the positrons $\beta^+$ within trap 12. In one embodiment, the trapping electric field E may comprise a rotating electric field, i.e., an electric field E that rotates about the longitudinal axis 38 of trap 12, e.g., generally in the direction indicated arrow 40. See FIG. 2. The use of a rotating electric field E is advantageous in that it causes the positrons $\beta^+$ to be tightly confined along axis 38, which reduces positron loss (e.g., from annihilation with electrons) during confinement. During the confinement period, i.e., during the time wherein the trapping (e.g., rotating) electric field E is applied, positrons $\beta^+$ will continue to be produced by the positron emitters within the source material 16 and/or moderator 18. Such additional positrons $\beta^+$ will then be trapped or confined by the combined electric and magnetic fields E and B within the interior region 14 defined by trap 12.

After a desired number of positrons $\beta^+$ have been produced, moderated, and confined within trap 12, the collected positrons $\beta^+$ may be released from trap 12. In one embodiment, the positrons may be released from trap 12 by operating the voltage source 34 to apply the "release" voltage function to the various components comprising trap 12. By way of example, in one embodiment, the release voltage function may comprise reducing or removing the voltage potential placed on one or both of the end cap electrodes 22, 24. The application of the release voltage function causes the positrons to be released via one or both of the end cap electrodes 22 and 24. The released positrons $\beta^+$ may then be used as desired.

As will be described in further detail below, another embodiment of the method and apparatus shown and described herein may be used to produce protons and trap them for later release. Protons may be produced in-situ (e.g., via a $\gamma$–p reaction) in a manner similar to that used to produced positrons $\beta^+$. Proton production via the $\gamma$–p process has a high probability from interactions with photons $\gamma$ from photon source 20 having energies greater than about 10 MeV. In fact, depending on the particular type of source material 16 that is utilized, both positrons and protons may be produced as a result of photon bombardment. Protons so produced may be stored in trap 10 and released for later use in a manner similar to that for storing and releasing positrons $\beta^+$.

A significant advantage of the apparatus 10 for producing and storing positrons $\beta^+$ (and/or protons) is that it results in high positron production and trapping rates. For example, the ability to produce the positrons in-situ, i.e., within the trap 12 itself, minimizes positron loss (e.g., through annihilation with electrons) that invariably occurs in moving positrons from a separate source (e.g., an accelerator or isotopic source) to a storage device. In addition, the positron emitters that are formed within the source material 16 and, optionally, moderator 18 have comparatively high positron production rates (e.g., on the order of $10^{16}$ positrons per second per gram of activated material or greater). In addition, the comparatively short half-lives of the positron emitters (e.g., on the order of minutes or hours) eliminates issues associated with long-term radioactive contamination.

Still other advantages are associated with the moderator material. For example, in conventional positron production/storage systems, a significant quantity of positrons are lost due to annihilation within the moderator material. However, the screen-like moderator(s) 18 in the present invention are specially configured to minimize annihilation losses while still providing the desired degree of moderation. Moreover, in embodiments wherein the moderator 18 comprises a material that will result in the formation of positron emitters in response to photon bombardment, the additional positrons $\beta^+$ produced by the positron emitters formed within moderator 18 helps to make-up for positrons lost to annihilation events.

Additional advantages may be realized where a rotating electric field E is used, in combination with magnetic field B, to confine the positrons $\beta^+$. For example, because the rotating electric field E causes the positrons $\beta^+$ to be tightly confined around the central axis 38 of trap 12, fewer positrons will be lost to the moderator material 18 and/or source material 12. In addition, the voltage on the interior moderator grids 18 may be varied to minimize the average positron momentum in the area between each moderator grid 18 and to assure a low momentum in the region of the positron plasma. Moreover, the comparatively high-density of the confined positron plasma achievable by the rotating electric field confinement process tends to further reduce positron loss during the trapping period.

Having briefly described certain embodiments of apparatus for producing and storing positrons and protons, as well as some of their more significant features and advantages, various exemplary embodiments of the positron and/or proton production and storage apparatus as well as methods for producing and storing positrons and/or protons will now be described in detail.

Referring back now to FIG. 1, one embodiment of apparatus 10 for producing and storing positrons $\beta^+$ may comprise a trap 12 that defines an interior region 14 therein. In the embodiment shown and described herein, trap 12 may comprise a generally cylindrically-shaped structure that extends along a central or longitudinal axis 38. Alternatively, other shapes and configurations are possible, as would become apparent to persons having ordinary skill in the art after having become familiar with the teachings provided herein. The trap 12 may be divided or segmented into a plurality of sections to facilitate the production of a rotating electric field E in the manner described herein. By way of example, in one embodiment, the trap 12 is divided into four segments 42, 44, 46, and 48, as best seen in FIG. 2, although a greater or lesser number of segments may be provided. The segments 42, 44, 46, and 48 may be substantially identical in size to one another and may be arranged so that they are substantially concentric with central axis 38. The various segments 42, 44, 46, and 48 of trap 12 are electrically insulated from one another to allow different voltage potentials to be applied to the various segments in the manner that will be described in further detail herein. In one embodiment, each of the segments 42, 44, 46, and 48 is electrically insulated from an adjacent segment by an insulating member 50. Alternatively, insulating members 50 could be eliminated and a gap provided between adjacent segments.

Trap 12 may comprise any of a wide range of sizes depending on the requirements of the particular application as well as the sizes of the various ancillary equipment and devices (e.g., vacuum chamber and magnets) that may be required or desired for the operation of the positron production and storage apparatus 10. In addition, the overall size of the trap 12 will also be dependent on the Brillouin and space-charge limits for the positron density expected, as would be apparent to persons having ordinary skill in the art after having become familiar with the teachings provided herein. Consequently, the present invention should not be regarded as limited to a trap 12 having any particular size. However, by way of example, in one embodiment, trap 12 may have an overall diameter 52 of about 5 cm, and an overall length 54 of about 70 cm.

As mentioned above, it is generally preferred, but not required, that trap 12 be fabricated from a source material 16 that, when activated by photon bombardment (schematically illustrated by arrows γ) become positron emitters that produce positrons $\beta^+$ (e.g., via the γ,n process). That is, trap 12 and source material 16 will be one and the same. Alternatively, if the trap 12 is not fabricated from a source material 16, then a separate source material 16 may be provided, as would become apparent to persons having ordinary skill in the art after having become familiar with the teachings provided herein. For example, in one such alternative embodiment, the source material 16 may comprise a separate component or element that is positioned within the interior chamber 14 defined by the trap 12. In another variation, the source material 16 could comprise a thin sheet-like element or foil. The sheet-like element or foil source material 16 may be provided as a separate element within the interior chamber 14 defined by trap 12, or could be placed on (i.e., conformed to) the surface of trap 12. In yet another variation, the source material 16 could comprise a coating or plating that is deposited on the surface of trap 12 by any of a wide range of coating processes.

Regardless of the particular arrangement of the trap 12 and source material 16, i.e., regardless of whether the source material 16 comprises trap 12, is provided as a separate element within region 14, or comprises a coating on the surface of trap 12, positrons $\beta^+$ can be produced by bombarding the source material 16 with photons γ. That is, if the photons γ have sufficient energies (i.e., above the photonuclear threshold for the particular source material 16), the bombardment process will cause neutrons to be ejected from atoms within the source material 16. The resulting neutron-deficient nuclei will decay into more stable material through positron decay (e.g., according to the well-known γ,n process). During the decay period, which is a function of the half-life of the material, positrons $\beta^+$ are continually produced. As discussed below, elements such as copper produce relatively high yields of positrons at energies from the photonuclear threshold of about 9 MeV.

Positron production rates and production energy can be varied based on the elemental composition used for production and the positron energy spectrum for the source material 16. Generally speaking, the source material 16 should be 1) easily machinable or workable, 2) electrically conductive, and 3) have an excitable nucleus with a sufficiently long half-life that large numbers of positrons can be produced, and 4) produce a positron energy that minimizes moderator requirements. Almost all metals produce positrons based on the γ,n reaction and therefore would be candidates for source material 16. The primary differences relate the half-life of the activated material and the energy distribution of the positrons. Half-lives can range from seconds to years with average positron energies ($E_{av}$) ranging from about 0.4-1.5 MeV.

Generally speaking, the source material 16 should have a half-life in a range of hours to days (i.e., to maximize positron production without long-lived contamination) and produce positrons having a relatively low average energy (i.e., to minimize moderation requirements). Suitable materials for the source material 16 include nickel ($^{58}$Ni→$^{57}$Ni 100%, 35.6 hr half life, $\beta^+$ yield—positron work function—1.4 eV) as metallic nickel or as a nickel-tungsten alloy (i.e., NiW). Copper and/or various alloys thereof (half-life of $^{64}$Cu (12.7 hours) and $E_{av}$ (approximately 0.3 MeV−$E_{max}$−0.651)) is also a good material. Further, $^{62}$Cu (Eav=1.3 MeV, half-life 9.74 minutes) is also present in copper.

Figure 3:
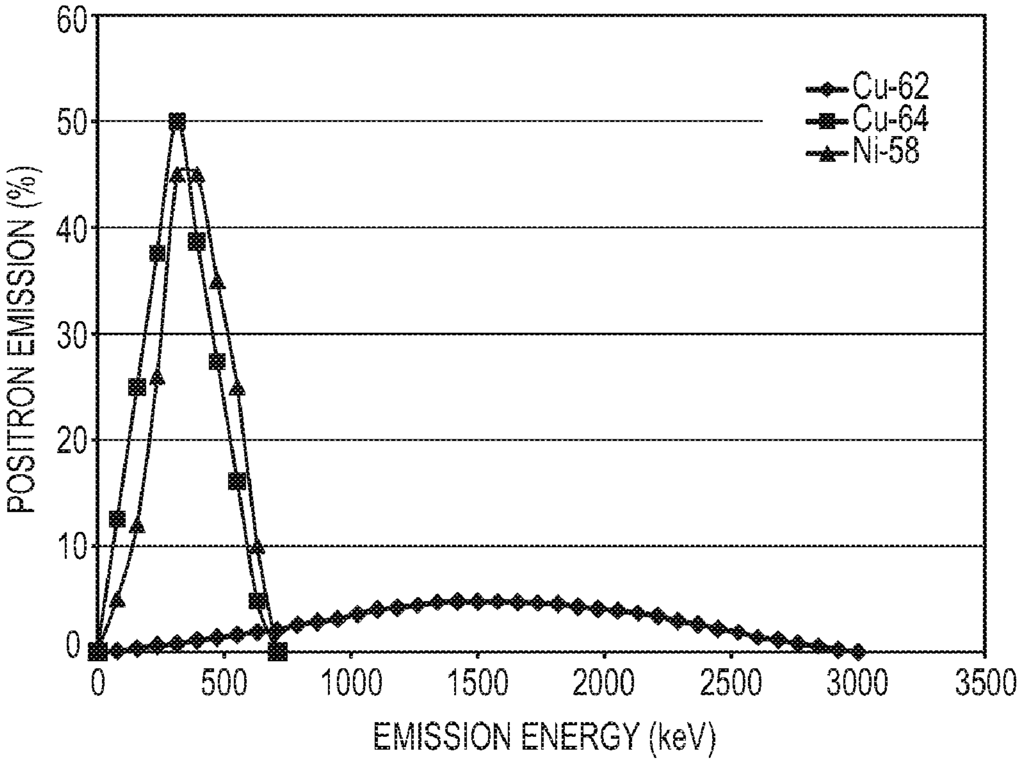
FIG. 3 illustrates the positron emission yields for two different copper isotopes ($^{62}$Cu and $^{64}$Cu) and $^{58}$Ni as a function of emission energy.

FIG. 3 depicts the positron emission yields for two different copper isotopes ($^{62}$Cu and $^{64}$Cu) and $^{58}$Ni as a function of emission energy. As illustrated in FIG. 3, $^{62}$Cu is distributed over the energy range to 2.9 MeV and $^{64}$Cu over the range to about 0.65 MeV. For short term irradiations (up to about 1 hr), $^{62}$Cu would be the primary source whereas for longer irradiations (up to about 100 hours) $^{64}$Cu will be the primary source with a contribution from $^{62}$Cu, which is at secular equilibrium. For long term positron production, $^{58}$Ni is a better option for high yield long term positron production because of the long half-life and low $E_{av}$.

Based upon extensive (γ,n) measurements for copper, calculations were performed to determine the production rate of positrons per gram of copper present in a cell for activation. Positron production was calculated based on HpGe detector and corrections performed for detector efficiency for a 1 cm copper foil 25 μm thick (0.223 g). The positron production rate for a foil having a surface area of about 1 cm$^2$ and a thickness of about 25 μm is 7.6×10$^7$ positrons/s for a 3 minute activation). The total number of positrons generated from this activation is about 6.6×10$^{10}$ positrons over a period of about 90 minutes. Consequently, if the same foil specimen were activated until equilibrium was reached (about four half-lives or about 38 minutes), the total production rate of positrons would be 1.3×10$^9$ positrons per second and the total yield over about 3 hours if the irradiation were stopped at 38 minutes would be 1.3×10$^{12}$ positrons per 0.223 g of copper at equilibrium or about 6×10$^{12}$ positrons per second per gram. About half as many would be generated from $^{64}$Cu; however the production period would run over about 100 hours. Therefore, the production rate would be about 1×10$^{13}$ positrons per second per gram. Consequently, if a 24-hour activation were performed with 100 g copper, the total production would be about 8.6×10$^{19}$ positrons/day.

For nickel, $^{59}$Ni is 68% of natural nickel and the $^{58}$Ni produced has a 100% $\beta^+$ yield. Consequently, it would be expected to not reach secular equilibrium until about 250 hours after activation began, would have a high yield with productions similar to the copper and much longer lived.

One consideration about the material selected for source material 16 relates to the effect of long term irradiation on the stability of the source material 16. Displacement analysis calculations indicate that long term activation of the source material 16 would not affect the stability or material properties of the source material 16 as the fraction of atoms affected is small compared to the total number present (i.e., 1 mole of copper is 63.5 g or 6.02×10$^{23}$ atoms). If activated with positrons produced at the rate of 2.6×10$^{15}$ positrons per day, as noted above, for 1000 days, the total number of atoms affected would be 2.6×10$^{18}$ or 1 atom in 2.24×10$^7$. This is far below the number needed to result in changes to the material properties of the metal.

The positron production and storage apparatus 10 may also be provided with moderator 18 positioned adjacent the source material 16. Moderator 18 moderates positrons $\beta^+$ emitted by the positron emitters within the source material 16. Generally speaking, the moderator 18 should be capable of moderating the positrons $\beta^+$ down to thermal energies so that the positrons $\beta^+$ can be effectively trapped or confined by the electric and magnetic fields (E and B) existing within the interior region 14 of trap 12. In the embodiment shown and described herein, the moderator 18 may comprise one or more generally cylindrically-shaped screen-like structures positioned adjacent trap 12 so that they are generally concentrically positioned with one another, as best seen in FIGS. 1 and 2. Alternatively, moderator 18 may comprise other configurations, as would become apparent to persons having ordinary skill in the art after having become familiar with the teachings provided herein. Consequently, the present invention should not be regarded as limited to the particular moderator configuration shown and described herein.

More specifically, and in the embodiment shown and described herein, each screen-like moderator 18 may comprise a plurality of individual segments 56, 58, 60, and 62, as best seen in FIG. 2. The segments 56, 58, 60, and 62 may be arranged so that they are substantially concentric with central axis 38 of trap 12. The various segments 56, 58, 60, and 62 of each moderator 18 should be electrically insulated from one another to allow different voltage potentials to be applied to the various segments 56, 58, 60, and 62 in the manner that will be described in further detail herein. In one embodiment, each of the segments 56, 58, 60, and 62 of the screen-like moderator 18 is electrically insulated from adjacent segments by insulating member 50. Alternatively, insulating members 50 could be eliminated and a gap provided between adjacent segments.

While the embodiment shown and described herein comprises two screen-like moderators 18 (i.e., comprising eight individual segments 56, 58, 60, and 62) arranged in a generally nested, concentric configuration, a greater or fewer number of moderators 18 may be used, as would become apparent to persons having ordinary skill in the art after having become familiar with the teachings provided herein. Consequently, the present invention should not be regarded as limited to any particular number of moderators 18.

Moderator 18 may comprise any of a wide range of materials (e.g., tungsten) suitable for providing the desired degree of moderation. In addition, it is generally preferred, but not required, that moderator 18 also comprise a material that contains atoms that, when activated by photon bombardment, become positrons emitters in order to increase the positron yield. By way of example, in one embodiment, the moderator 18 may be fabricated from nickel, nickel-tungsten alloys, and copper. Silver and various alloys thereof may also be used.

Figure 4:
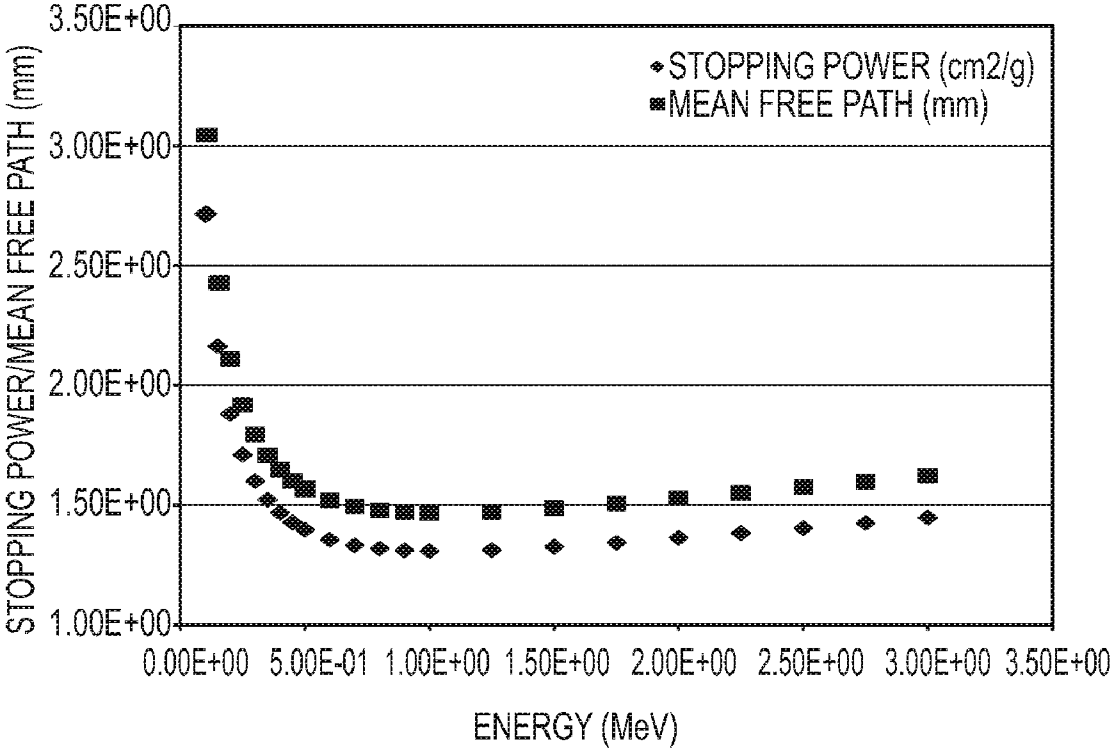
FIG. 4 illustrates the stopping power of copper for electrons over a range of energies.

FIG. 4 depicts the stopping power of copper (e.g., having a density of about 8.9 $g/cm^3$) for electrons over a range of energies. The data presented in FIG. 4 were determined by the ESTAR code, which is available from the National Institutes of Standards (NIST). The positron response is expected to be similar. These data indicate that the mean free path of electrons (and, by extension, positrons) is relatively consistent at energies beyond 0.5 MeV at about 1.5 mm. Consequently, the moderator 18 chosen for use with the present invention should be a fraction of this thickness to prevent significant annihilation with the moderator material. Nickel has a similar density and would be expected to behave similarly unless alloyed with tungsten.

As briefly discussed above, moderation of the positrons down to a thermal energy where the positrons can be trapped is a significant issue as it results in a significant loss of positrons due to annihilations with the moderator material. The current approach to positron moderation is to use annealed tungsten ribbons with thicknesses of 25 μm and to utilize the positron work function of the tungsten (−2.8 eV) to prevent interaction with the moderator material after the positron has been re-emitted from the tungsten. The typical moderation efficiency for tungsten is approximately $2\times10^{-4}$. Although tungsten is not a positron emitter, other materials have negative work functions (e.g., nickel, positron work function, −1.4 eV) and, as discussed, are excellent positron emitters. Consequently, overlapping grids of either nickel or a nickel-tungsten alloy will provide excellent moderation, and when activated, provide an additional source of positrons $\beta^+$.

The positron work function for copper is expected to be low and/or similar to silver. Consequently, copper or silver, which also have high positron yields and reasonable half lives could also be used as the moderator 18. In any event, in addition to the positron work function, a voltage is applied to the moderator 18 (e.g., by voltage source 34 via phase sequence filter 36) and there is a higher voltage applied to the end caps 22 and 24 (described below) that results in the moderated positrons moving back and forth between the end caps 22, 24 and the moderator 18.

Based upon the positron stopping powers for copper or nickel, the individual grid wire thickness for the screen-like moderator 18 may be about 25 microns or less in order to minimize positron annihilations within the moderator material 18. If tungsten wire is used for the screen-like moderator 18, then the wire thickness may be in the range of about 10-20 microns.

Trap 12 may also comprise one or more end cap electrodes 22 and 24 positioned adjacent the open ends 26, 28 of trap 12. End cap electrodes 22 and 24 may be used to confine and/or selectively release positrons $\beta^+$ that are confined or trapped within the interior chamber 14 of trap 12. Trap 12 may also comprise a pair of compensating electrodes 30 and 32 positioned between the open ends 26, 28 of trap 12 and the end cap electrodes 22 and 24, as best seen in FIG. 1.

The end cap electrodes 22 and 24, as well as the compensating electrodes 30 and 32 may be fabricated from any of a wide range of materials (e.g., metals and metal alloys) suitable for the particular application. By way of example, in one embodiment, the end cap electrodes 22, 24, and the compensating electrodes 30, 32 are fabricated from stainless steel.

As mentioned above, the positron production and storage apparatus 10 may also be provided with a voltage source 34 capable of providing various voltage potentials on the various components of the positron production and storage apparatus 10. The apparatus 10 may also be provided with a phase sequence filter 36 to allow a rotating electric field E to be established, as will be described in greater detail below. Voltage source 34 may be electrically connected to the end cap electrodes 22, 24, as well as to the compensating electrodes 30 and 32, as best seen in FIG. 1. Phase sequence filter 36 may be electrically connected between voltage source 34 and the various segments 42, 44, 46, and 48 of trap 12, as best seen in FIG. 2. In addition, phase sequence filter 36 may be electrically connected to various ones or all of the segments 56, 58, 60, and 62 of the individual screen-like moderators 18.

Voltage source 34 and phase sequence filter 36 may comprise any of a wide range of systems and devices that are now known in the art or that may be developed in the future that are suitable for placing various voltage potentials on the various components of the apparatus 10 in accordance with the teachings provided herein. However, because voltages sources and phase sequence filters suitable for use with the present invention are known in the art and could be readily provided by persons having ordinary skill in the art after having become familiar with the teachings provided herein, the particular voltage source 34 and phase sequence filter 36 that may be utilized with the present invention will not be described in further detail herein.

The positron production and storage apparatus 10 may be operated as follows to produce and store for later release a quantity of positrons $\beta^+$. Before proceeding with the description, it should be noted that many ancillary devices and components may be required or desired for the operation of the positron production and storage apparatus. However, because such ancillary devices and components are well-known in the art and could be readily provided by persons having ordinary skill in the art after having become familiar with the teachings provided herein, and because a detailed description of such ancillary devices and components is not necessary to understand the present invention, such ancillary devices and components are not described in detail herein.

In one operational scenario, the trap 12 may be positioned within a suitable vacuum chamber (not shown) that has been evacuated to a high vacuum. The vacuum chamber may also be provided with a magnet, such as an electromagnet (also not shown), suitable for creating a magnetic field B within the interior region 14 defined by trap 12. In the embodiment shown and described herein, the magnetic field B is generally axially oriented, i.e., so that the field lines thereof are generally parallel to the longitudinal axis 38 of trap 12, as best seen in FIG. 1. The magnetic field B may have any of a wide range of strengths depending on the overall size and configuration of the apparatus 10, the density of the positron plasma to be confined, and other factors, as would become apparent to persons having ordinary skill in the art after having become familiar with the teachings provided herein. Consequently, the present invention should not be regarded as limited to magnetic fields having any particular strengths. However, by way of example, in one embodiment, the magnetic field B may have a strength of in a range of about 0.1 Tesla to about 1 Tesla. Magnetic fields having strengths of about 10 Tesla or greater may also be used in applications involving high-density positron plasmas.

As mentioned above, several different methods may be used to activate the source material 16 and/or moderator material 18. The photons γ used to activate the source material 16 and/or moderator material 18 should have energies sufficient to active the atoms contained in the source material 16 and/or moderator 18. For example, in an embodiment wherein the source material 16 and moderator 18 comprise copper, photons γ having energies in the range of about 10-20 MeV will be sufficient to activate the various isotopes of copper comprising the source material 16 and moderator 18, thereby causing them to emit positrons $\beta^+$. The photons γ may be produced by photon source 20 positioned adjacent trap 12 so that photons γ produced thereby will impinge or bombard the source material 16 and moderator 18.

Photon source 20 may comprise any of a wide variety of systems and devices suitable for producing photons γ having energies suitable for activating the source material 16 and, optionally, moderator 18. However, because suitable photon sources are known in the art and could be readily provided by persons having ordinary skill in the art after having become familiar with the teachings provided herein, the particular photon source 20 that may be utilized in one embodiment of the present invention will not be discussed in further detail herein.

The source material 16 and moderator 18 may be activated in-situ. That is, the materials 16 and 18 may be bombarded by photons γ when the trap 12 is contained in the vacuum chamber (not shown). In another variation, the trap 12 (comprising the source material 16 and moderator 18) may be bombarded with photons γ just before it is placed within the vacuum chamber. In yet another variation, just the source material portion 16 of trap 12 may be activated (i.e., bombarded with photons γ), then positioned within trap 12, which may then be used to moderate, confine, and release the positrons $\beta^+$.

The positrons $\beta^+$ are confined within the interior region 14 of trap 12 by the magnetic field B and the electric field E. In the embodiment shown and described herein, the electric field E is produced by or emanates from the various elements of apparatus 10 that are connected to the voltage source 34 and/or phase sequence filter 36. For example, in one embodiment, the trap 12 may be operated in the manner of a conventional Penning-Malmberg trap, in which negative voltage potentials are applied to trap 12 and the end cap electrodes 22 and 24. Negative potentials may also be placed on various ones of the screen-like moderators 18 and the compensating electrodes 30 and 32 in order to provide an electric field E suitable for confining the positrons $\beta^+$. In such a configuration, voltage potentials of about −350 volts and a magnetic field B having a strength in a range of about 0.1 Tesla to about 0.2 Tesla will be suitable for confining positrons $\beta^+$ within trap 12. Increased numbers of positrons, i.e., a positron plasma having an increased density, can be confined by increasing the voltage potentials and magnetic field strengths. Of course, during the confinement period, positrons $\beta^+$ will continue to be produced by the positron emitters within the source material 16 and moderator 18, with the additional positrons $\beta^+$ also being moderated by moderator 18. Confined positrons $\beta^+$ may be released from the interior region 14 of trap 12 by, for example, removing the negative voltage potential from one or both of the end cap electrodes 22, 24, and compensating electrodes 30, 32.

In another embodiment, the positron plasma may be trapped by utilizing a rotating electric field E, i.e., an electric field E that rotates about the longitudinal axis 38 of trap 12, e.g., generally in the direction indicated by arrow 40. See FIG. 2. The use of a rotating electric field E is advantageous in that it causes the positrons $\beta^+$ to enter a Trivelpiece-Gould plasma mode which causes the positrons to be more tightly confined along axis 38, which reduces positron loss during confinement. A rotating electric field E can be produced by connecting a phase sequence filter 36 between voltage source 34 and the trap 12. In addition, one or more of the moderator grids 18 may also be connected to phase sequence filter 36, as best seen in FIG. 1. By way of example, in an embodiment wherein the trap 12 comprises four individual segments 42, 44, 46, and 48. Each of the moderator grids 18 also comprise four individual segments 56, 58, 60, and 62. Phase sequence filter 36 may be used to apply phase-shifted sinusoidal voltages to the various segments of trap 12 and moderator grids 18 in order to create the rotating electric field E. In the embodiment shown and described herein, the sinusoidal voltages applied to adjacent segments of trap 12 and moderator grids 18 are phase-shifted by about 90°, i.e., so that opposed ones of the segments are phase-shifted by about 180°. The frequency of the sinusoidal voltage functions may be maintained at a constant frequency or may be varied.

The sinusoidal voltage functions applied to the various segments of trap 12 and moderator grid(s) 18 may comprise a wide range of voltages depending on the particular application, the expected density of the positron plasma and other factors, such as the dimensions of the trap 12, the positron mean free path and energy, and the strength of the magnetic field. Generally speaking, smaller traps and higher positron densities will require the use of higher voltages and higher frequencies, whereas larger traps and lower positron densities will allow for substantial reductions (e.g., by several orders of magnitude) in the required voltages and frequencies. Consequently, the present invention should not be regarded as limited to any particular voltages or frequencies. By way of example, in one embodiment for a trap 10 having a length 54 of about 70 cm and a plasma radius of about 0.5 cm, and a magnetic field in a range of about 0.1 to about 0.2 Tesla, the RMS value of the sinusoidal voltage may be about 1000 volts (V). The frequency of the sinusoidal voltage functions may be about 4 kilohertz (kHz).

It should be noted that the phased (e.g., sinusoidal) voltage potentials need not be applied to all of the screen-like moderators 18, but could only be applied to the outer-most screen-like moderators 18, i.e., those screen-like moderators located near the trap 12. Other screen-like moderators, i.e., those closer to the longitudinal axis 38 of trap 12, need not be connected to the voltage source 34 and/or phase sequence filter 36. In addition, the maximum potential (i.e., RMS voltage) applied to the moderator grids 18 need not be identical, but could vary. For example, the maximum potential applied to the outer-most moderator grid 18 may be slightly greater than those applied to the inner moderator grids 18 in order to minimize the average positron momentum in the area between each moderator grid 18 and to assure a low momentum I the region of the positron plasma.

While the trap 12 and moderators 18 comprise four individual segments, configurations having a greater or lesser number of segments may be used to generate the rotating electric field E, as would become apparent to persons having ordinary skill in the art after having become familiar with the teachings provided herein. Consequently, the present invention should not be regarded as limited to configurations having any particular number of segments.

After a desired number of positrons $\beta^+$ have been produced, moderated, and confined within trap 12, the collected positrons may be released from trap 12. In one embodiment, the trapped positrons may be released by lowering or removing the voltage potential on one or both of the end cap electrodes 22 and 24, in the manner already described.

As mentioned above, the method and apparatus of the present invention may also be used to produce and trap protons. Protons may be produced by the source material 16 itself (e.g., via a high energy $\gamma$–n process) in response to bombardment by high energy photons $\gamma$, typically having energies in a range of about 10 MeV to about 22 MeV. If it is desired to produce and store protons, the source material 16 should be selected so as to result in the production of protons. Source materials suitable for proton emission are listed in Table I, along with the energy ranges where significant production of protons will occur. The data presented in Table I were obtained from the Brookhaven National Nuclear Data Center EXFORS reaction database.

TABLE I

| Isotope | High Cross Section Energy Range |
|---|---|
| $^{59}Co$ | 10-14 MeV |
| $^{58}Ni$ | 13-21 MeV |
| $^{63}Cu$ | 14-20 MeV |
| $^{64}Zn$ | 18-22 MeV |

If protons are desired to be trapped for later release, the electric and magnetic fields E and B will need to be modified to efficiently confine the protons, as would become apparent to persons having ordinary skill in the art after having become familiar with the teachings provided herein.

Having herein set forth preferred embodiments of the present invention, it is anticipated that suitable modifications can be made thereto which will nonetheless remain within the scope of the invention. The invention shall therefore only be construed in accordance with the following claims:

The invention claimed is:

1. Apparatus for producing and storing positrons, comprising:

a trap defining an interior chamber therein, said interior chamber containing an electric field and a magnetic field, said trap comprising:

a source material, said source material comprising atoms that, when activated by photon bombardment, become positron emitters that produce positrons; and a moderator positioned adjacent said source material, said moderator moderating positrons emitted by the positron emitters activated within said source material; and a photon source positioned adjacent said trap, photons produced by said photon source bombarding said source material to produce the positron emitters, positrons from the positron emitters and moderated positrons from said moderator being confined within the interior chamber of said trap by the electric and magnetic fields.

2. The apparatus of claim 1, wherein said source material defines at least a portion of the interior chamber of said trap.

3. The apparatus of claim 2, wherein said source material comprises a generally cylindrically-shaped structure, the cylindrically shaped structure of said source material defining the interior chamber of said trap.

4. The apparatus of claim 3, wherein said moderator is positioned within the interior chamber of said trap.

5. The apparatus of claim 4, wherein said moderator comprises a generally cylindrically-shaped screen-like structure, the generally cylindrically-shaped screen-like structure being disposed within the generally cylindrically-shaped source material so that they are in generally concentric relationship with one another.

6. The apparatus of claim 5, wherein said moderator comprises a plurality of generally cylindrically-shaped screen-like structures, the plurality of generally cylindrically-shaped screen-like structures being disposed within the generally cylindrically-shaped source material so that they are in generally concentric relationship with one another.

7. The apparatus of claim 1, further comprising a voltage source, said voltage source being electrically connected to said source material, the electric field within the interior chamber of said trap emanating from said source material.

8. The apparatus of claim 7, wherein said voltage source is electrically connected to said moderator, said voltage source applying a voltage to said moderator.

9. The apparatus of claim 7, further comprising an end-cap electrode positioned adjacent the interior chamber defined by said trap, said end cap electrode being electrically connected to said voltage source, said voltage source being operable to apply a containment voltage function to said end cap electrode to confine positrons within the interior chamber of said trap.

10. The apparatus of claim 9, wherein said voltage source is operable to apply a release voltage function to said end cap electrode to release positrons from the interior chamber of said trap.

11. The apparatus of claim 1, further comprising a magnet positioned exterior to said trap, said magnet producing the magnetic field within the interior chamber of said trap.

12. The apparatus of claim 11, wherein the magnetic field within the interior chamber of said trap has a strength of about 1 Tesla.

13. Apparatus for producing and storing positrons, comprising:

a generally cylindrically-shaped trap defining an interior chamber therein, said trap comprising a source material including atoms that, when activated by photon bombardment, become positron emitters that produce positrons;

a moderator positioned within the interior chamber defined by said generally cylindrically-shaped trap, said moderator moderating positrons emitted by the positron emitters activated within the source material;

a voltage source electrically connected to said trap, said voltage source causing an electric field to be established within the interior chamber defined by said trap; and a magnet positioned adjacent said trap so that at least a portion the interior chamber defined by said trap is contained within a magnetic field produced by said magnet.

14. The apparatus of claim 13, wherein said moderator comprises a generally cylindrically-shaped screen-like structure positioned within the interior chamber.

15. The apparatus of claim 13, wherein said moderator comprises a plurality of generally cylindrically-shaped screen-like structures positioned within the interior chamber so that they are positioned in a generally concentric, nested relationship with one another.

16. The apparatus of claim 15, wherein said plurality of generally cylindrically-shaped screen-like structures comprises eight individual screen-like structures.

17. The apparatus of claim 13, wherein the generally cylindrically shaped trap comprises a plurality of sections that are electrically insulated from one another, and wherein said voltage source comprises at least two output terminals, the at least two of the plurality of sections being connected to the output terminals of said voltage source.

18. The apparatus of claim 13, wherein the generally cylindrically shaped trap comprises four sections that are electrically insulated from one another, each of the four sections being electrically connected to said voltage source, said voltage source producing voltage functions that cause the electric field to rotate around a longitudinal axis of the generally cylindrically shaped trap.

19. The apparatus of claim 18, wherein the voltage functions produced by said voltage source comprise sinusoidal voltage functions and wherein the four electrically insulated sections of said trap comprise substantially equal sizes in generally opposed relationship around the longitudinal axis of the generally cylindrically shaped trap, the sinusoidal voltage functions applied to opposed ones of the insulated sections being phase shifted by about 180°.

20. The apparatus of claim 19, wherein an RMS voltage of each of the sinusoidal voltage functions is about 1000 volts.

21. The apparatus of claim 19, wherein a frequency of each of the sinusoidal voltage functions is about 4 kHz.

22. The apparatus of claim 1, wherein said source material comprises one or more selected from the group consisting of copper, nickel, silver, and alloys thereof.

23. The apparatus of claim 1, wherein said moderator comprises one or more selected from the group consisting of copper, nickel, tungsten, silver, and alloys thereof.

24. Apparatus for producing and storing positrons, comprising:

a trap defining an interior chamber therein;

electric field generation means operatively associated with said trap for producing an electric field within the interior chamber of said trap;

magnetic field generation means operatively associated with said trap for producing a magnetic field within the interior chamber of said trap;

a source material positioned within the interior chamber defined by said trap, said source material comprising atoms that, when activated by photon bombardment, become positron emitters that produce positrons;

a moderator positioned adjacent said source material, said moderator moderating positrons emitted by the positron emitters activated within said source material; and a photon source positioned outside said trap so that photons produced by said photon source bombard said source material to produce the positron emitters, positrons from the positron emitters and moderated positrons from said moderator being confined within the interior chamber of said trap by the electric and magnetic fields.

25. Apparatus for producing and storing positrons, comprising:

a trap defining an interior chamber therein, said interior chamber being adapted to contain an electric field and a magnetic field therein;

a source material provided within the interior chamber of said trap, said source material comprising atoms that, when activated by photon bombardment, become positron emitters that produce positrons;

a moderator positioned adjacent said source material, said moderator moderating positrons emitted by the positron emitters activated within said source material; and a photon source positioned exterior to said trap so that photons produced by said photon source bombard said source material to produce the positron emitters, positrons from the positron emitters and moderated positrons from said moderator being confined within the interior chamber of said trap by the electric and magnetic fields.

26. A method for producing and storing positrons, comprising:

providing a trap defining an interior chamber therein, said trap comprising a source material having atoms that, when activated by photon bombardment, become positron emitters that produce positrons;

establishing an electric field within the interior chamber defined by the trap;

establishing a magnetic field within the interior chamber defined by the trap; and bombarding the source material with photons, the photons activating atoms of the source material to produce the positron emitters, positrons from the positron emitters being confined within the interior chamber of the trap by the electric and magnetic fields.

27. The method of claim 26, further comprising providing a moderator within the interior chamber of the trap and adjacent the source material, the moderator moderating positrons emitted by the positron emitters.

28. The method of claim 26, further comprising rotating the electric field about a longitudinal axis of the trap.

29. The method of claim 26, wherein the source material is removable from the trap and wherein bombarding the source material with photons comprises bombarding the source material with photons at a location removed from the trap, followed by positioning the source material within the trap after bombardment.

30. The method of claim 26, wherein the source material comprises an integral portion of the trap and wherein bombarding the source material with photons comprises bombarding the trap with photons.

31. The method of claim 26, further comprising releasing positrons from the interior chamber of the trap.

32. The method of claim 31, wherein releasing positrons from the interior chamber of the trap comprises reconfiguring the electric field within the interior region of the trap.

33. The method of claim 26 wherein the trap comprises a plurality of sections that are electrically insulated from one another and wherein establishing an electric field within the interior chamber of the trap comprises placing voltage functions on the plurality of sections of the trap.

34. The method of claim 26, wherein the trap comprises a generally cylindrically shaped structure having four sections that are electrically insulated from one another and wherein establishing an electric field within the interior chamber of the trap comprises placing voltage functions on each of the four sections.

35. The method of claim 34, further comprising rotating the electric field about a longitudinal axis of the generally cylindrically shaped trap.

36. The method of claim 35, wherein rotating the electric field comprises placing phase-shifted sinusoidal voltage functions on the four electrically insulated sections.

* * * * *